(12) United States Patent
Mengato

(10) Patent No.: US 8,512,349 B2
(45) Date of Patent: Aug. 20, 2013

(54) APPARATUS FOR MEASURING DEPTH OF A BONE OPENING AND RELATED METHOD

(76) Inventor: Richard A. Mengato, Pittsburgh, PA (US)

( * ) Notice: Subject to any disclaimer, the term of this patent is extended or adjusted under 35 U.S.C. 154(b) by 963 days.

(21) Appl. No.: 12/001,844

(22) Filed: Dec. 13, 2007

(65) Prior Publication Data

US 2009/0157088 A1 Jun. 18, 2009

(51) Int. Cl.
| A61B 17/58 | (2006.01) |
| A61B 17/60 | (2006.01) |
| A61B 1/00 | (2006.01) |
| A61B 5/103 | (2006.01) |
| A61B 5/117 | (2006.01) |
| A61F 2/00 | (2006.01) |
| G01B 1/00 | (2006.01) |
| G01B 5/00 | (2006.01) |
| G01B 3/22 | (2006.01) |

(52) U.S. Cl.
USPC .............................. 606/102; 33/512; 33/836

(58) Field of Classification Search
USPC ............ 606/102; 33/512, 827, 836; 600/587
See application file for complete search history.

(56) References Cited

U.S. PATENT DOCUMENTS

| 2,241,451 | A | * | 5/1941 | Fist ................................ 600/591 |
| 3,738,355 | A | * | 6/1973 | Salvatore ....................... 606/102 |
| 3,958,570 | A | | 5/1976 | Vogelman et al. |
| 4,016,867 | A | * | 4/1977 | King et al. ..................... 600/591 |
| 4,033,043 | A | | 7/1977 | Cunningham |
| 4,243,040 | A | | 1/1981 | Beecher |
| 5,013,318 | A | * | 5/1991 | Spranza, III ................... 606/102 |
| 5,171,248 | A | * | 12/1992 | Ellis ............................... 606/102 |
| 5,242,448 | A | | 9/1993 | Pettine et al. |
| 5,356,382 | A | * | 10/1994 | Picha et al. .................... 604/105 |
| 5,486,183 | A | * | 1/1996 | Middleman et al. ........... 606/127 |
| 5,702,401 | A | * | 12/1997 | Shaffer .......................... 606/102 |
| 5,928,243 | A | | 7/1999 | Guyer |
| 6,152,894 | A | * | 11/2000 | Kubler ............................. 604/22 |
| 7,134,216 | B2 | * | 11/2006 | Rupp et al. ....................... 33/512 |
| 7,444,756 | B2 | * | 11/2008 | Kim ................................. 33/512 |
| 7,895,762 | B2 | * | 3/2011 | Kim et al. ........................ 33/512 |
| 2006/0207118 | A1 | | 9/2006 | Kim |
| 2006/0224161 | A1 | * | 10/2006 | Bhattacharyya ............... 606/102 |
| 2007/0106181 | A1 | * | 5/2007 | Mangiardi et al. ............. 600/587 |

* cited by examiner

*Primary Examiner* — Kevin T Truong
*Assistant Examiner* — David Bates
(74) *Attorney, Agent, or Firm* — Eckert Seamans Cherin & Mellott, LLC; Arnold B. Silverman

(57) ABSTRACT

Apparatus for measuring bone depth for determining the length of fastener to be employed in medical treatment of the bone includes an elongated inner bone probe having a bone-engaging portion and a plurality of first manually-engageable elements secured thereto. An outer sleeve overlies at least a portion of the inner bone probe and is movable with respect thereto. A second manually-engageable element is secured to the outer sleeve. The first and second manually-engageable elements may be generally ring-shaped, so as to facilitate insertion of a user's fingers. The apparatus is structured to have the bone-engaging portion of the inner bone probe pass through an opening in the bone and engage the distal exterior surface in intimate contact as a result of the first manually-engageable elements being engaged and urged away from the bone. The outer sleeve is moved generally toward the bone so as to achieve contact between the distal end of the outer sleeve and the proximal exterior surface of the bone. A reading of desired fastener length may then be made. Other embodiments of the gauge employing different configurations of the two main components and additional functional features, as well as adaptors, which facilitate retro-fitting structural features, of the present invention into prior art devices. Associated methods are provided.

18 Claims, 12 Drawing Sheets

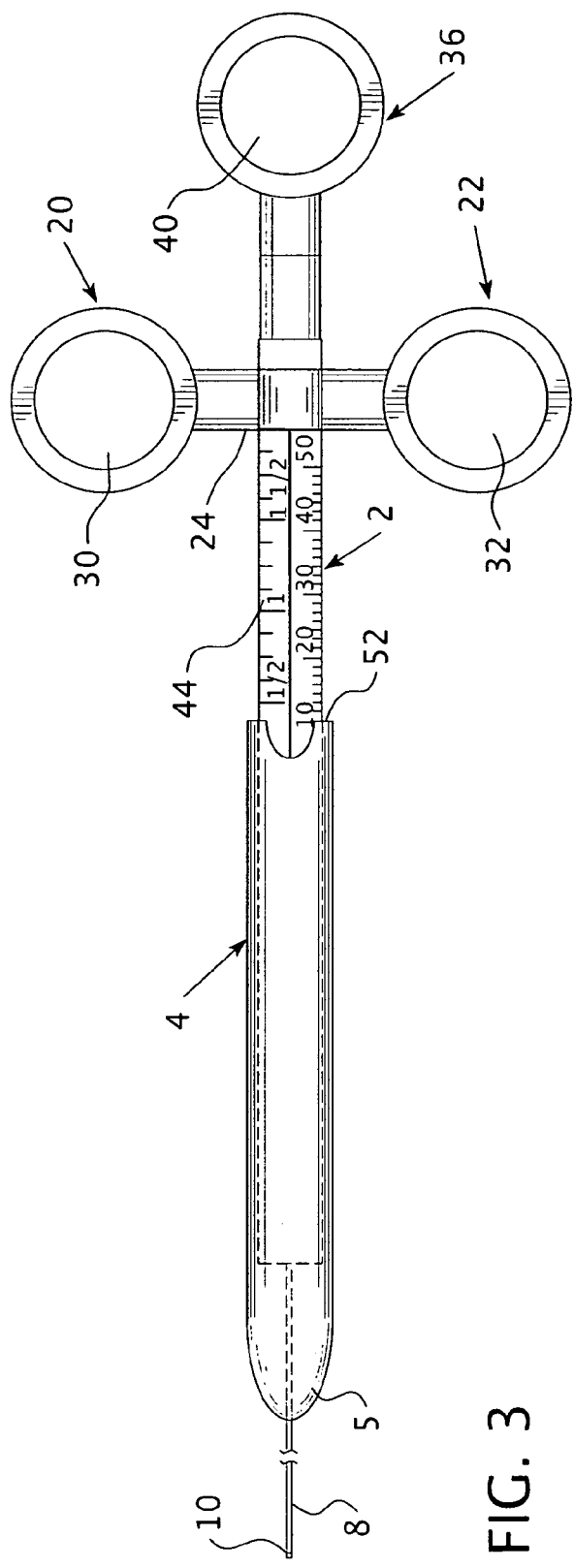
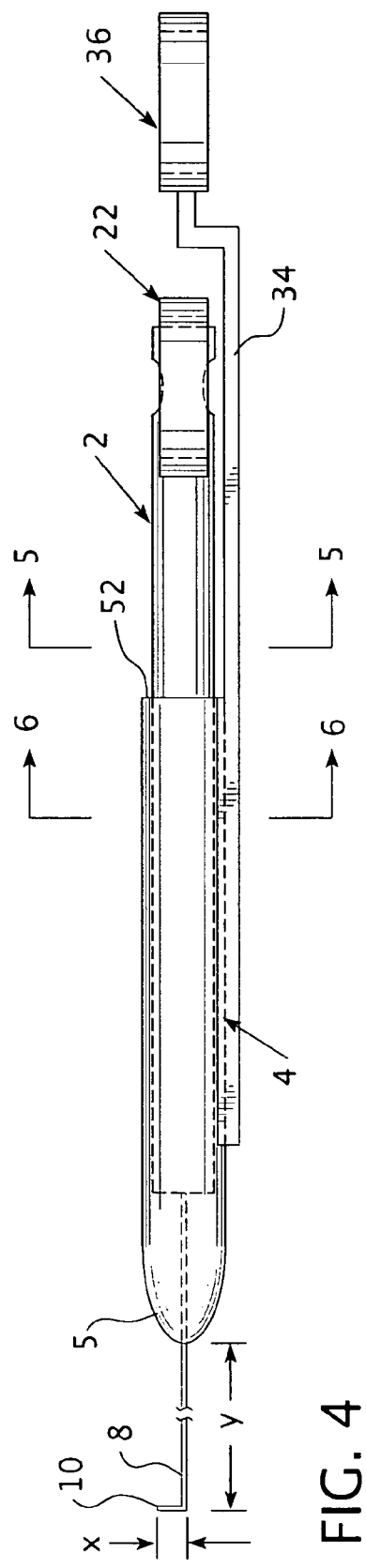
FIG. 3
FIG. 4

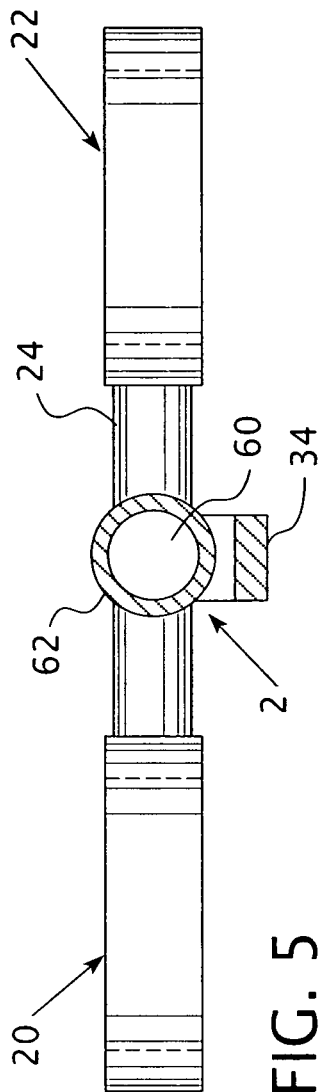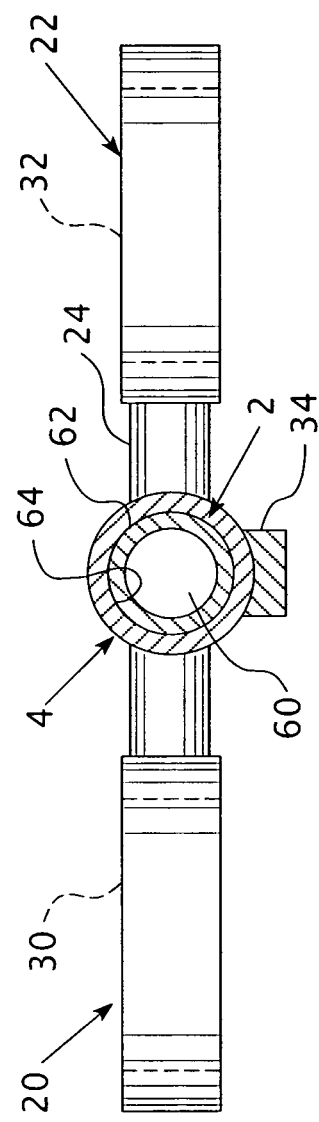
FIG. 5
FIG. 6

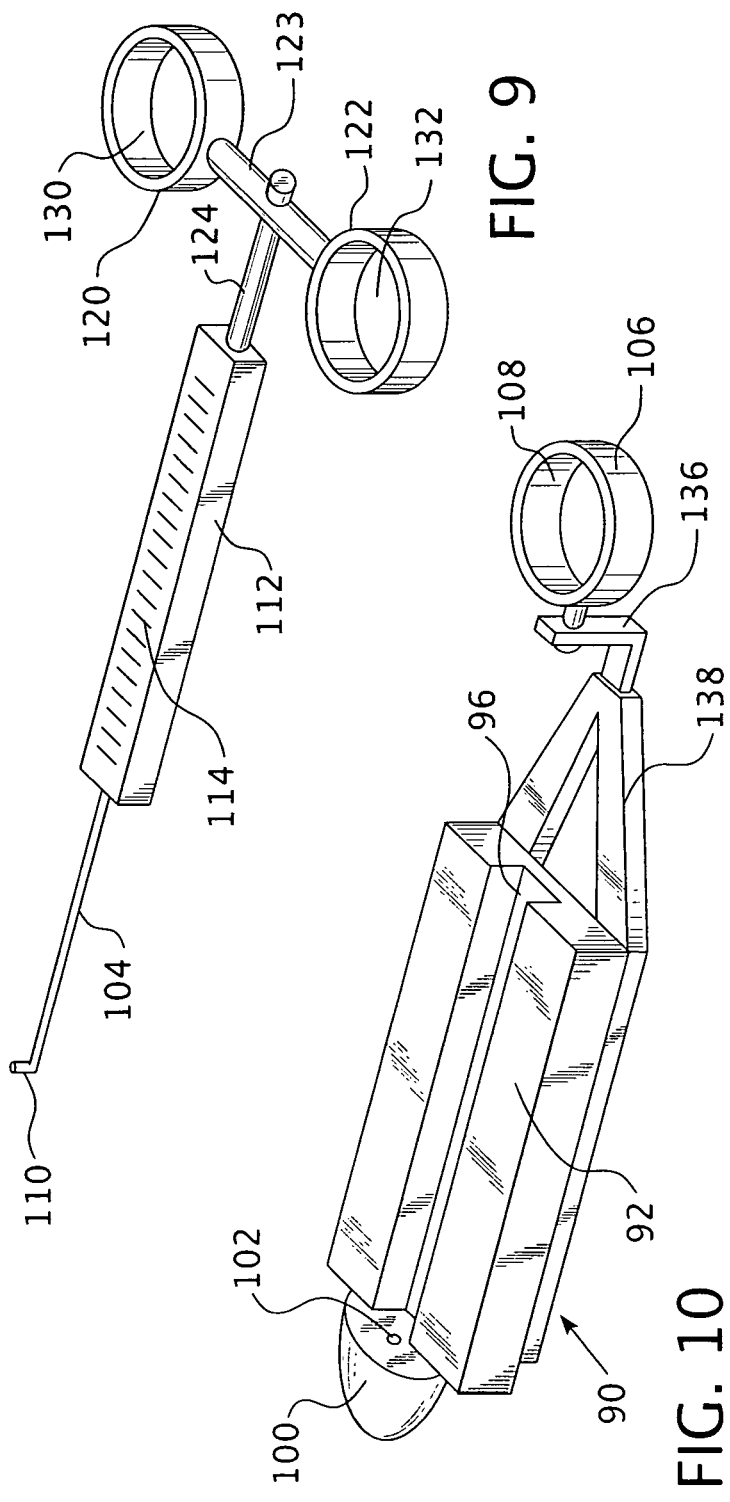
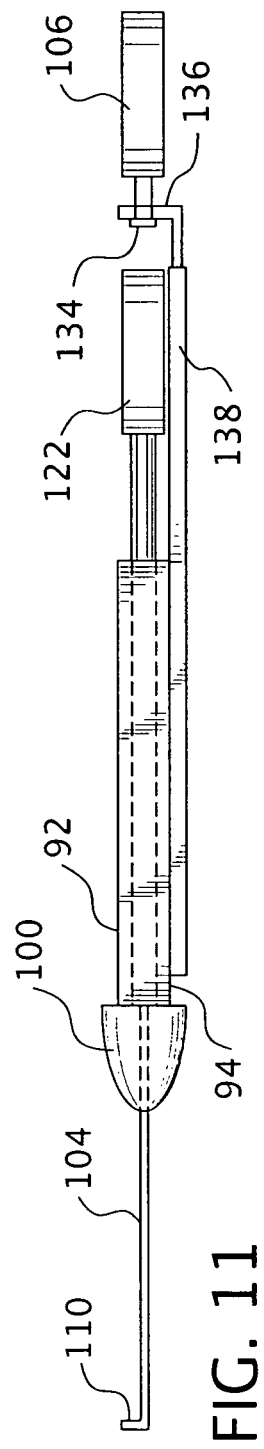
FIG. 9
FIG. 10
FIG. 11

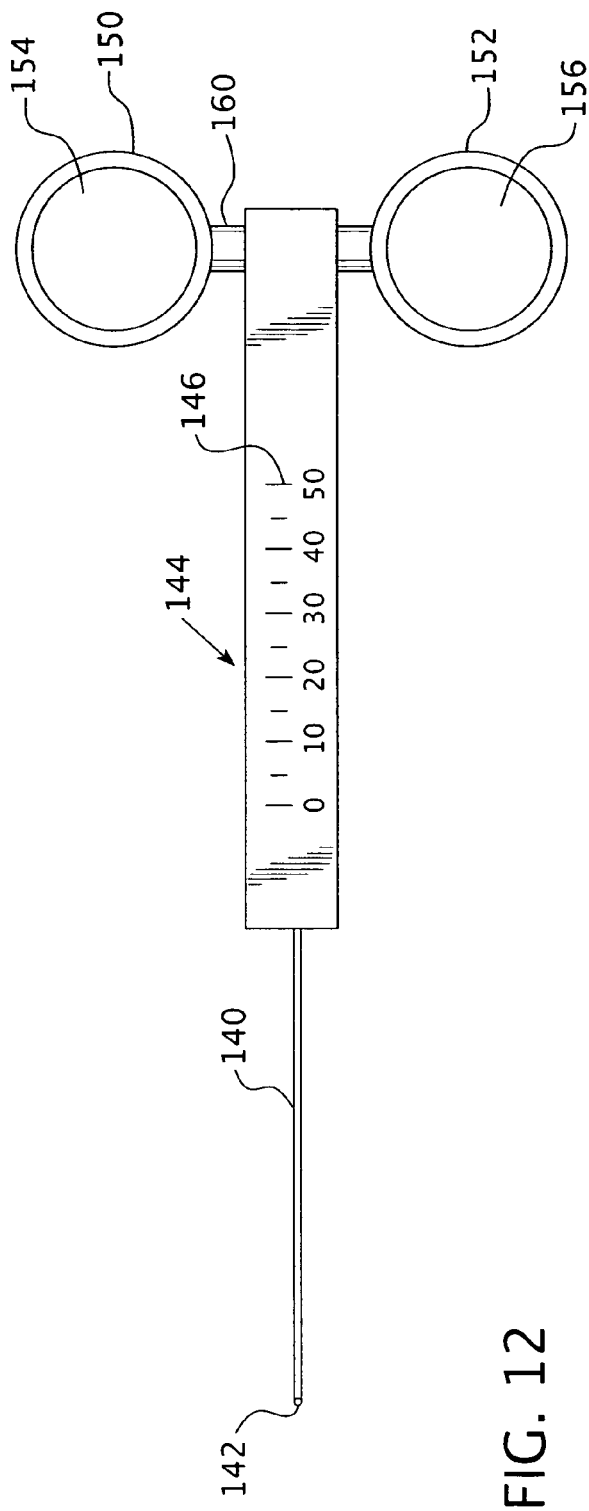
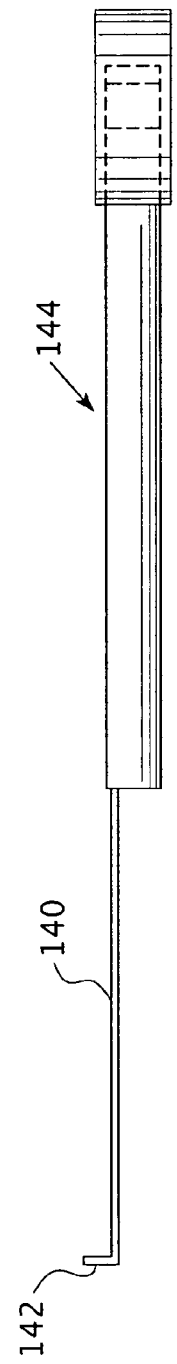
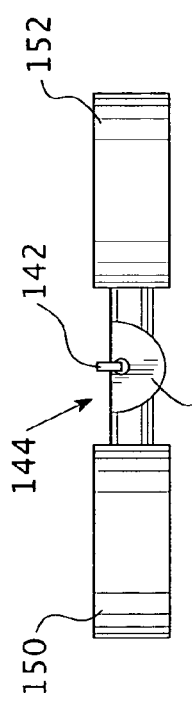
FIG. 12
FIG. 13
FIG. 14

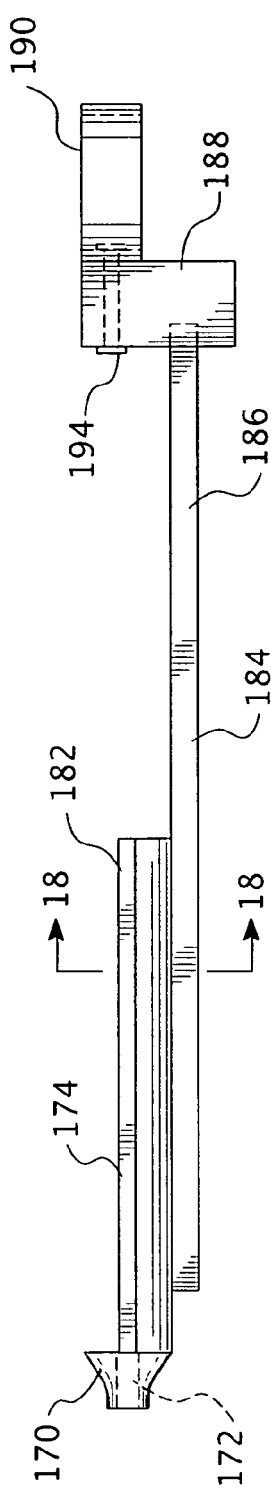
FIG. 15
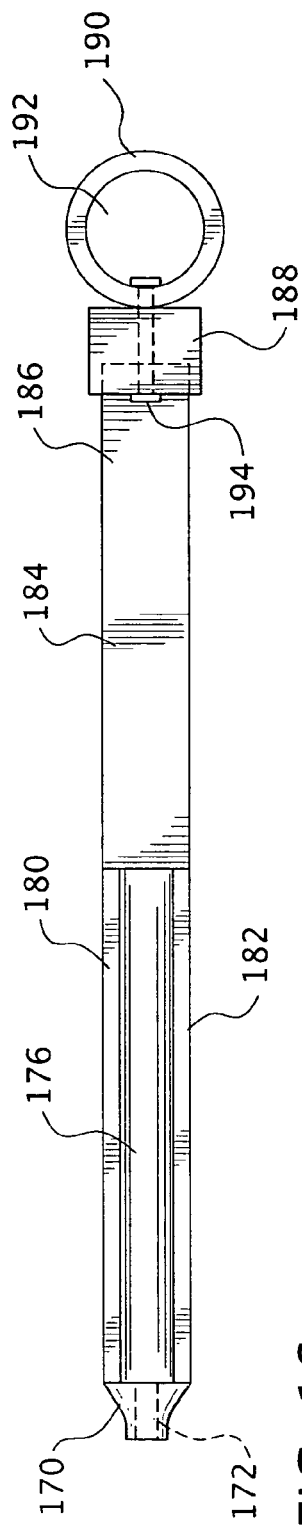
FIG. 16
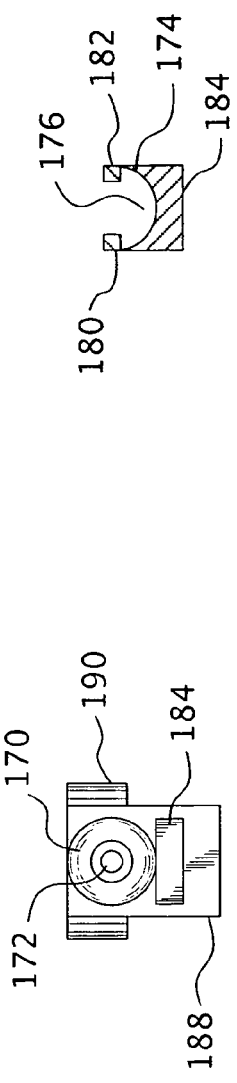
FIG. 17
FIG. 18

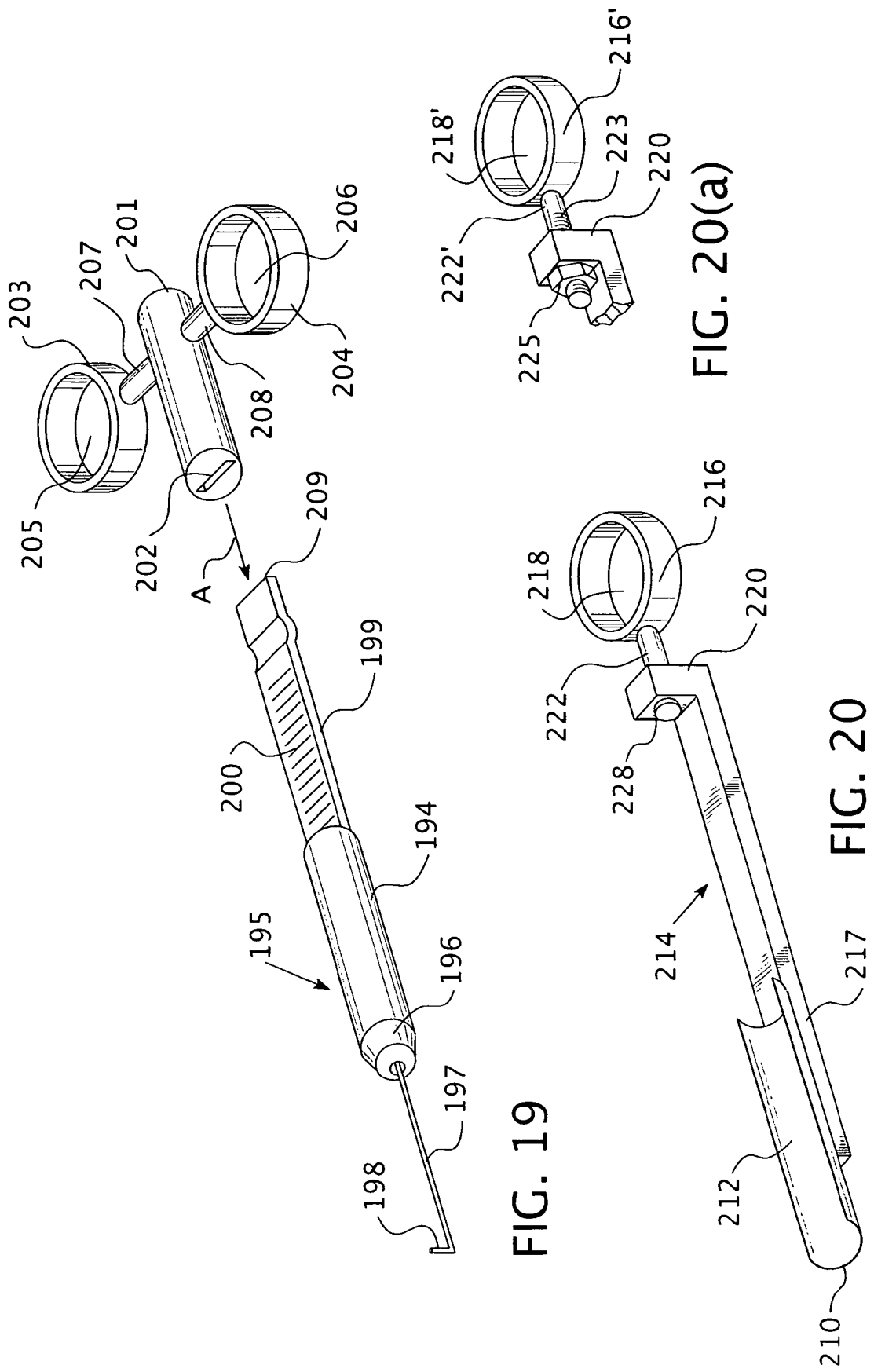

APPARATUS FOR MEASURING DEPTH OF A BONE OPENING AND RELATED METHOD

BACKGROUND OF THE INVENTION

1. Field of the Invention

The present invention relates to an improved apparatus and associated methods of measuring the length of an opening in a bone, so that an appropriate fastener for use in medically restoring the bone may be selected.

2. Description of the Prior Art

It has been known in both human and veterinary uses to employ a depth gauge to measure the depth of a hole in a bone. A fastener, such as a pin or a screw, for example, of appropriate length can be employed in a surgical procedure in facilitating repair or reconstruction of bones, which have suffered traumatic injuries or are damaged as the result of congenital deformities or are the result of disease or otherwise make it desirable to assist a bone during healing.

A variety of such surgical procedures are performed on human bones by orthopaedic, plastic, ear nose and throat, maxillofacial, neuro-, and general surgeons. These include a variety of emergency and elective procedures. Similar procedures are employed by veterinarians in their work.

Whether fixing a fractured bone, correcting a congenital or acquired bone deformity, or merely removing a portion of bone to allow access to deeper tissues and structures, many of the surgical procedures involve placement of screws or pins or nuts and bolts into a bone with or without plates or rods for added support. These screws are usually metallic, but in some cases, they may be made from other materials, such as polymeric materials capable of being ultimately broken down and absorbed by the body. Such screws are placed for fixation or securing of pieces of bone directly, or to secure other hardware, such as metal plates or rods, to the bones involved as part of a more complex construct designed to hold two or more pieces of bone together.

Several techniques are commonly employed. One or more of these may be done any one particular surgery. Isolated screws may be placed directly into one fragment of bone or placed across or through two or more bone fragments to hold them directly together. One or more screws may be placed first through a portion of bone and then through other hardware, such as metal plates or rods, which have openings or holes, to accommodate passage of the screw so that the resulting construct holds two or more pieces of bone together as one. Screws may be placed first through hardware such as a plate lying on the outer surfaces of two or more pieces of bone and then into the bone, to secure the plate to the bone fragments effecting a construct to "bridge" and secure together the bone fragments. This may apply to two or more pieces of bone which have been separated by traumatic fracture, or bones which have been cut apart and re-aligned by the surgeon to correct a deformity (a so-called corrective osteotomy).

Usually a precise length of a screw must be known to assure good purchase of the screw over its length and to assure that the screw is not so prominent as to cause a problem with other tissues on which it might impinge. Therefore, techniques for precise measurement of appropriate screw length must be employed. There are a number of recognized surgical complications which have occurred from screws which are too short leading to insufficient fixation and "pulling out" of the fixation hardware and loss of position of repaired bones. In other cases, screws which are too long have resulted in damage to normal structures, such as tendons, which have ruptured as a result of wear against screw ends protruding through bones.

In a general way, many bones can be viewed as a cylindrical structure with a thicker, stronger outer wall of the cylinder (known as the cortex) and a softer middle or inside portion (known as the medullary cavity). Bone can almost be viewed as a thick-walled hollow cylinder, though the softer middle does have some substance. Screws are usually placed in one of two fashions, so-called 1) "unicortical" and 2) "bicortical." In unicortical placement, the screw extends through the outer cortex of one side of the bone and protrudes into the inner cavity. In bicortical placement, the screw is placed across the entire width of the bone, so that the screw enters through the outer surface or cortex of one side of the bone, extends through the inner cavity and then extends to, or just through, the outer edge or cortex of the bone across from the entry site. In general, bicortical placement results in a stronger purchase of the screw in the bone, but situations exist where only unicortical placement is possible or, in some cases, desirable. The screws are usually placed by preparing or drilling a pilot hole across the bone at the desired location for the screw. In bicortical placement, this pilot hole is drilled through the near or entry site cortex, through the medullary cavity and out through the exit site cortex (opposite the entry hole). In unicortical placement, this pilot hole is drilled through the near or entry site cortex and into or through the medullary cavity, but not through the cortex opposite the entry site (the so-called distal cortex). Even with unicortical placement, sometimes the depth of the "partial" bone hole is measured in order that the screw placed does not "bottom out" and the head protrude too far above the entrance hole.

In the process of fixation of two or more bone fragments, such as occurs with a fracture or break of a bone, the fragments are usually assembled or repositioned by manipulation, manually or with instruments, to reconstitute the normal shape of the bone. This is called "reduction of the bone or fracture." The fragments are then held together manually by the surgeon and/or his or her assistants or held by clamps designed for that purpose. Screws may then be placed across the construct usually extending from the cortical surface of one bone fragment, across the plane of the fractured surface(s) and then extending to and through the outer cortical surface of the second bone fragment thus securing the two fragments together. In this case, the pilot hole will traverse the cortex of the first bone piece, cross the plane of the fracture, and then traverse the cortex of the second bone piece. Alternatively, or in conjunction with direct screw placement, after appropriate reduction of the bone, a metal plate designed for this purpose is placed on the outer cortical surface of the bone, so that a portion of the plate overlies or is in contact with each of the bone fragments. Screws are then placed through holes spaced along the plate for that purpose, into each segment of the plate adjacent to a bone fragment, into and across the adjacent bone fragment. The holes within the plate are usually contoured or countersunk within the plate to allow the head of a screw to sit within the depression of the countersink and exert pressure against the plate to secure it. These countersunk holes also decrease the prominence of the screw head above the plate. This construct allows the plate to "bridge" across and support the various bone fragments to hold them in proximity, so they are able to heal by the normal biological processes. The metal fixation devices maintain the bones in proper alignment for the normal or desired ultimate shape of the healed bone while the healing process takes place. In some situations, a rod may be placed through the inner cavity portion of the bone once all of the fragments have been reduced or aligned. One or several screws may be placed through the outer surface of the bone, through holes in the rod for that purpose, placed at appropriate positions along the length of the rod, and then out through the rod and through the cortical bone on the other side of the rod. This links together the rod and the various bone fragments, again for the purpose of maintaining alignment and allowing appropriate healing of the bone.

The screws, plates, and rods used in such a manner are typically made of metal of various types, but other materials have also been used, including some types which are ultimately absorbed by the body once the healing process has occurred. It is important to place screws of appropriate length to properly engage the bone and adjunctive fixation devices, but not so long as to impinge unnecessarily on other tissues.

In most cases, placement of screws involves drilling a pilot hole into or through the bone(s) and measuring the depth of the hole or the distance from the outer edge of the bone at the entry site of the hole to the outer edge of the bone at the exit site of the hole. The proper length of screw can then be inserted into the hole. The lengths and depths of such bone holes are measured by devices, which are commonly known in surgical parlance as "depth gauges." In cases where a plate is used for fixation, typically, the plate is set on the surface of the involved bone, and the pilot hole is made by passing the drill bit through an existing screw hole in the plate down to the surface of the outer cortex of the bone, and then drilling through the adjacent bone. The plate is maintained in position overlying the bone and the now present bone hole. The length of the opening between the bottom of the screw-hole in the plate and the exit hole of the bone is measured to provide a screw of the appropriate length to account for the thickness of the plate (and its screw hole), as well as the bone itself. The components of depth gauges are configured so as to nest within the holes of the metal plate and account appropriately for the thickness of the plate.

Usually, only one side of the involved bone is readily accessible or visible to the surgeon, so that the depth of the pilot hole must be determined by devices which access the pilot hole from one side. The diameter of the pilot hole is usually slightly smaller than the diameter of the screw to be used so that the threads of the screw can bite or obtain purchase in the bone adjacent to the hole and secure the screw. The mechanics of the appropriate sizes of screws for holding various types and sizes of bones and for use with various fixation devices has been determined in various studies by surgical scientists and vendors of such products and is fairly standardized. In orthopaedic surgery, most screws used vary between about 1 and 5 millimeters in diameter, for example. Lengths may vary from about 8 millimeters up to 10 centimeters and longer depending on the application. Lengths of 10 to 50 millimeters are very commonly used. In most situations, the length of the screw must be measured to within 1-2 millimeters of accuracy. These dimensions, the accessibility of the involved structures in the surgical field, and the situation of a sterile surgical setting do provide some constraint on the size, shape, and type of devices or depth gauges which might be used to measure the pilot holes described.

The ideal depth gauge should be accurate, simple to maneuver, and it should be easy to read the indicated depth. It must be easy to clean thoroughly and capable of being readily sterilized. The device should be easy and relatively inexpensive to manufacture, durable, and mechanically reliable. Ideally, the manipulation of the gauge in all its aspects should be possible with one hand. Oftentimes the surgeon using the gauge may require the other hand to help secure the limb or body part being addressed, to directly hold together the bones of the fracture being fixed, or to support clamps which are holding the fracture. The presence of blood and tissue fragments may interfere with motion of parts which might be more easily mobile in a less harsh environment. While a device which is reuseable after suitable cleaning is consistent with many of the instruments currently used in surgical procedures, designs of a depth gauge, which are suitable for one-time use, are also quite easily conceived. The constraints of anatomy and surgical exposure may limit the ability to position or manipulate the gauge.

A variety of devices, or depth gauges, exist or have been proposed for measuring the length or depth of holes in bone. The prior art devices in current practice are generally based on mechanical principles. These devices exhibit many of the "ideal" characteristics listed hereinbefore and have been used actively in surgical practice for several decades. In general, such mechanical devices have the advantage of relative simplicity for manufacturing and use, durability, and familiarity for operation by those accustomed to working with tools. While some specialized designs exist to function with some specific designs of fixation devices, such as a gauge, which might attach directly to a fixation device and allow measurement of screw length as well as function as a guide for screw placement, most depth gauges are more universal in that they can be used to measure any bone hole. Various sizes of gauges are available, as appropriate, for holes of certain diameter and depth ranges, so that, for instance, gauges for measuring screws used in surgery on bones of the hand are generally scaled differently from those used to measure those of the femur, although the general principles and mechanics of the design may be similar.

Referring to FIGS. 1 and 2, which show examples of prior art gauges, most of the prior art designs in current use can be described as having a nested design in which an outer barrel or sleeve 1 slides over, or relative to, an inner arm or barrel 3 which has a narrow probe 5 at one end. The probe portion usually has a small "J" or hook-like portion 7 at its tip. The width of the hook-like portion 7 of the "J" is limited because the widest dimension of the probe (width of the shaft of the probe 5 plus the width of the protruding "hook" 7) must fit through the pilot hole in the bone, which, in many applications, is only between 1 and 3.5 millimeters wide. The actual extended or hook portion 7 can only be a part of this total width so that the entire width of the tip fits through the pilot hole, but there is enough protrusion of the "hook" to serve as a place to "catch" on the edge of the bone hole. The probe 5 is inserted through the pilot hole and the hook 7 is used to "catch" or grapple on to, the outside edge of the bone at the exit point of the pilot hole. There are other devices which have been proposed, such as, for example, those of Bhattachayyra (U.S. Published Patent Application No. 2006/0224161 A1), which have posited more complex arrangements for "hooking" the far end of the pilot hole. The prior art probe is maintained in position, "hooked" to the opposite side of the bone. The outer barrel or sleeve 1 of the gauge is then advanced against the bone of the outer edge of the entrance site of the hole. The two sides of the bone hole are thus defined and with proper calibration of the relative positions of the probe portion 5 and the outer sleeve 1 portions of the gauge, a scale 9 established and marked on the gauge in its manufacture can be read to indicate the length/depth of the bone hole. The distal portion of the outer barrel 1 which contacts the bone of the near cortex, or entry hole site, usually has a tapered tip with a contour similar to a screw head, so that when a plate is used, the tip portion of the outer barrel can seat down in the screw hole in the plate, and the tip 11 of the outer barrel 1 contacts the depth of the screw hole where the screw head will actually contact the plate and thus accommodates for the thickness of the plate.

Most prior art designs, while useable, suffer significantly in terms of their maneuverability. The existing gauges are such that the proximal portion of the inner barrel portion of the gauge is either flat or a half-cylinder like shape. Usually there are notches or depressions near the end opposite to the probe, which are to accommodate finger holding of this end of the probe. They allow interdigitation of the thumb or fingers on a front notch and a posterior notch to facilitate grasp and manipulation of this element of the gauge. A scale is usually imprinted on one side of the surface proximal to the narrow bone probe for use in reading measurements. The outer barrel often has grooves or a roughened surface to aid in gripping and manipulation of that segment of the gauge.

In a simple description of use, the gauge is grasped with one hand and the probe portion is inserted into the bone hole, and "hooked" against the edge of the exit side of the hole, the outer barrel is advanced down against the near side of the bone, and a reading of screw length is made. While this overall concept is simple and straightforward, the actual manipulation is often difficult. Use is really a five-step process:
1) Inserting the probe through the bone hole;
2) "Hooking" the end of the probe on the exit side of the hole;
3) Maintaining the gauge and probe in a steady "hooked" position;
4) Advancing the outer barrel against the entry side of the hole while maintaining the "hooked" position; and
5) Reading the measurement.

A detailed examination of these steps helps to understand the problems with current designs.

To use the prior art gauge, the gauge is grasped over the outer barrel and the proximal portion of the inner barrel/probe portion, using the thumb and several or all of the fingers in a manner similar to that used for grasping an object, such as a toothbrush or a table knife, for example. Alternatively, the gauge can be grasped in a similar manner, but only holding onto the proximal portion of the inner barrel. Holding the gauge in this manner, the probe is inserted into and through the pilot hole. When it is judged or felt that the end of the probe has traversed the hole, force is directed to lever the probe portion against the inner walls of the bone hole, and the probe is slowly withdrawn until the "J" hook is felt to catch on the far side of the hole. Maintaining pressure of the probe against the sidewalls of the hole while maintaining a gentle pull or tension in the direction of withdrawing the "hook" is necessary to keep the "J" from disengaging from the edge of the hole and withdrawing back through the pilot hole prior to making a measurement. This allows for positioning of the probe within the bone hole and securing the hook of the probe against the exit surface of the hole. Next, if the entire gauge was grasped, the hand grasping the gauge must be adjusted so that only the proximal portion of the inner sleeve/probe is being held, and the outer barrel is free to slide. Usually the middle, ring, and small fingers, or some combination thereof are curled around this proximal end to secure it and maintain the gauge and probe in a fixed position. Pressure of the probe against the sidewalls of the pilot hole and proximally directed tension on the "hook" must be maintained throughout this process to keep the probe "hooked." For one-handed use, while holding the probe portion in steady position, the thumb, or thumb and index finger of the grasping hand, is/are then slid or straightened in such a way as to move them toward the bone hole and use them to push against the proximal end of the outer barrel and advance or slide it over the inner probe until the outer barrel contacts the bone at the entry site of the hole. In this position, a marking on the outer barrel is aligned with the scale marked on the inner barrel, and a reading of length of the desired pin or screw can be made. For the less-preferred, two-handed use, while the first hand maintains position of the probe, the opposite hand is used to grasp the outer barrel and advance it into position. There are some minor variations in the exact shape and way of marking scales for the various gauges in current use, but they are all similar.

In practice, there are several difficulties with manipulation as described and as the gauge is designed to be operated.

Inserting the probe portion can sometimes be difficult if bone fragments or other tissues block part or all of the hole. Usually, this portion of use can be accomplished because, if needed, the whole gauge can be grasped firmly enough to wield it in a forceful manner.

During the phase in which the probe is being "hooked," the balance of forces to hold pressure on the sidewalls of the hole and slight withdrawal tension on the "hook" can be somewhat difficult to maintain with the type of grasp which must be used. The forces must be exerted in part or in whole by the wrist and arm rather than just movements of the fingers because the fingers are held in a nearly fully flexed position to maintain the grasp on the gauge itself. These forces of the wrist and arm are grosser with less fine control of force and position than those which are controlled just by finger motion.

Once the probe is positioned and "hooked" as described hereinbefore, maintaining the position of the hook with the grasping technique noted is of limited security because of the nature of holding a narrow, elongated structure in such manner. A good example of this instability can be demonstrated by holding the end of a pen opposite from the point by curling some combination of the middle, ring, and small fingers around it for support or even by pinching it between the thumb and one or several fingers. If one tries to push the point end of the pen to deflect it in another direction, it is fairly easy to deflect unless one is grasping along the majority of the barrel of the pen with more of the hand/fingers. Such grasp of the depth gauge is not possible except during insertion of the probe, as the outer barrel portion ultimately needs to be free to slide over the inner, probe portion. Again, the forces maintaining the gauge and probe in position must be largely exerted by the wrist and arm.

Other factors also contribute to difficulty in maintaining the position of the "probe/hook." The grasp of the "hook" is somewhat tentative due to the relatively small size of the "hook." The edge of the bone hole which is being hooked may be slightly rounded as well due to the nature of bone substance. These aspects contribute to making it relatively easy to cause the hook to disengage, and in fact, it is not unusual to have to reset the "hook" several times during the measuring process. These factors necessitate a way to provide fine control of the gauge to resist loss of position during measurements.

For one-handed use, it is biomechanically difficult to maintain a grasp on the proximal end portion of the probe, keeping lateral pressure of the end of the probe against the walls of the hole and proximal directed force (away from the hole) on the probe to keep the "hook" "set," and then, with the same hand, direct movement of the thumb or thumb/index finger toward the hole to advance the outer barrel. The competing forces of pushing toward the hole with part of the hand and pulling away from the hole with another part of the hand is difficult with the configuration of the usual gauges. This is in part again due to the fact that the probe position must be maintained in part by the relatively gross forces and control associated with wrist and arm muscles relative to those of the hand.

During the phase of advancing the outer barrel, because of the forces directed toward the hole, sometimes, the entire gauge including the probe portion is advanced so the "hook" is no longer against the edge of the exit hole. This necessitates resetting the "hook," or if not recognized, results in overestimating the length of the required screw. The force needed to hold the probe against the side walls of the hole to keep the probe "hooked" also can cause bending of the probe and to a small degree the rest of the inner barrel. This deformation can make it mechanically more difficult for the outer barrel to slide because of increased friction. Presence of blood and/or tissue fragments which may adhere to the gauge may also interfere with easy sliding of the outer barrel. The nature of the contrasting motions needed to maintain the position of the probe and advance the outer barrel when combined with these other factors can make it difficult to use current gauges.

Often, the surgeon must hold the inner barrel and probe in position with one hand and slide the outer barrel with the other hand to successfully make a measurement. This can be problematic if the other hand is needed to hold the fracture or is otherwise employed in the surgical procedure, such as holding other instruments. Even with two-handed use, it can sometimes be difficult to balance the forces as the motions of the probe and the outer barrel are still done by wrist and arm movements, while the fingers are just used to maintain grasp on the parts of the device.

The contours, configurations, and biomechanics of operation of depth gauges currently in use, while resulting in useable devices, leave room for significant improvements in design, particularly as it relates to the ability to grasp the device, the ability to manipulate the device in a more biomechanically optimal way for the human hand, and the ability to manipulate the device with one hand during the various stages of operation necessary to measure the length of a hole in bone.

Vogelman, U.S. Pat. No. 3,958,570, while not disclosing a depth gauge, discloses elements of a syringe including those of what in current medical and surgical practice is often referred to as a "control syringe." The syringe also consists of two main elements with an inner sleeve or plunger and an outer barrel, which acts as a container for substances which are withdrawn into the syringe or ejected out of the syringe. These elements are also slidably connected. Vogelman discloses the placement of rings on the sleeves with one ring on the plunger and two rings on the outer sleeve or barrel. These allow firmer grip on the syringe and allow the plunger to be pushed with "considerable force." In fact, syringes with such ring attachments are in common use in the medical field and constitute the so-called "control syringe."

Guyer, U.S. Pat. No. 5,928,243 discloses a device with features typical of depth gauges which are currently used in the field of orthopaedic and other surgeries. The device includes a body, or outer barrel, and an inner sleeve, or shaft, which includes a probe portion. The two pieces are slidably connected and the inner shaft has markings which allow for measurement of the depth of bone holes. Typically, various sizes of such gauges are available with appropriate dimensions to make measurements for the sizes of screws typically used in surgical practice. The depth gauge of Guyer discusses a device very representative of those in current use and can be thought of as a "reversed" or "inverted" syringe. With a syringe, the outer barrel provides, in essence, a cannula for sliding of the plunger portion of the syringe. The barrel also contains any fluids or substances which are injected or withdrawn into the syringe. In its common usage the outer barrel also essentially contains a "probe" which in practice, is a needle. To use the syringe, the probe and outer barrel are set into position by manually advancing the needle into the site for injection (or site of withdrawal in the case of blood sampling) by gripping the barrel to which it is attached and using the barrel as a handle to manipulate the needle. The barrel and needle are then supported in position, and the plunger is advanced in the case of injection and withdrawn in the case of sampling. Advancing the plunger is usually done by pushing on the cap of the plunger with the thumb; although, a finger could be used. On simple syringes, flanges on the sides of the outer barrel allow counter-pressure against the advancing plunger by placing two fingers against the flanges. In a "control syringe," the flanges on the outer barrel and the cap of the plunger are replaced by rings which allow greater control and support and easier movement of the involved parts. The rings allow easier, one-handed use in most cases. In a depth gauge, the action is reversed. The inner sleeve and probe of the depth gauge corresponds to the outer barrel and needle of the syringe, and the outer barrel of the depth gauge most closely approximates the action of the plunger or inner barrel of the syringe. The inner sleeve and probe are positioned and set in place, and the outer barrel is then slid over the inner sleeve to achieve the final set position, which allows a measurement to be read from the gauge. In the syringe, the outer barrel and probe/needle are set, and the inner barrel (plunger) is advanced.

Novel features of the current invention include incorporation of ring handles in a particular and novel configuration for manipulating portions of a depth gauge. These are incorporated in a specific arrangement of design which enables the user to easily manipulate the device with one hand in all phases of its use and to do so in a manner which best utilizes the inherent biomechanics of the human hand as it relates to its ability to provide fine motor control and sensory feedback, which contributes to that control.

Middleman, U.S. Pat. No. 5,486,183, and Beecher, U.S. Pat. No. 4,243,040 disclose devices for use in surgery in which a probe or instrument is passed through an outer cannula or sleeve and in which the outer sleeve is controlled by one or more attached ring handles to accommodate finger grip, and the central portion or probe is controlled with a single ring handle intended for manipulation by the thumb. Beecher also teaches a swiveling type of arrangement for a single ring handle to better accommodate position of the digit being used to operate that ring.

Pettine, U.S. Pat. No. 5,242,448, discloses a bone probe which demonstrates as part of it, a ring-type handle on the probe portion. Again, this would allow manipulation of that probe portion which is set up mechanically to move in a way similar to the central plunger on a syringe, i.e., by use of the thumb in the ring of the central element, to advance and retract that element.

Cunningham, U.S. Pat. No. 4,033,043, teaches a device for measuring the length of an opening which can be operated in a one-handed fashion by means of gripping handles and levers. The design is more complex and mechanically different than that of the current invention.

Bhattacharyya, U.S. Published Patent Application No. 2006/0224161 A1, discloses a depth gauge apparatus which essentially has three parts. There is an outer barrel or sleeve and an inner barrel, which includes a probe portion. These two pieces are nested and slide relative to one another. The third portion is a mobile "spreader" device which is used to expand the tip of the probe to facilitate its ability to "hook" onto the edges of a bone hole. This patent also shows the use of rings to control the various elements with one ring for each of the three main elements shown in the exemplary embodiment. The function of this device requires proximal withdrawal of the central spreader to expand the tip of the probe, holding the inner barrel down with the one ring shown attached to it, and then, while maintaining this position, the outer barrel must be advanced distally (toward the bone hole) utilizing the ring attached to it. With the configuration of this device, knowledge of the biomechanics of the hand would dictate that to operate this device, one would need to place the thumb in the ring for the spreader, and two fingers, most likely the index and middle fingers, each in one of the other two rings. Depending on the orientation of the scale for reading measurements, most likely, the index finger would be placed in the ring for the outer barrel and the middle finger in the ring for the inner sleeve. To operate this then requires the thumb to extend to withdraw the spreader. The middle finger then holds the inner barrel steady, and the index finger must then be extended to advance the outer barrel. This combination of movements, extending the thumb, holding the middle finger and its barrel steady, and extending the index finger and advancing its barrel, would likely prove quite awkward in practice. While it is feasible, it is not the optimal utilization of the mechanics of the hand.

There remains, therefore, a very real and substantial need for an improved bone depth gauge and associated method which may be easily employed by medical personnel using one hand to accurately measure the depth of a bone passageway.

SUMMARY OF THE INVENTION

The present invention has met the above-described needs. The apparatus is so designed that, employing three fingers of one hand and applying forces in directions which make it easy to manipulate, it will permit the rapid, efficient measurement of the depth of a bone hole that will predetermine with reasonable medical precision the size fastener to be employed.

The apparatus of the invention includes an elongated inner bone probe which terminates in a bone-engaging portion for engaging a distal portion of the bone exit opening. A plurality of first manually-engageable elements of the bone probe are structured to be engaged and employed in moving the probe through the bone entry and exit openings and engaging the exterior distal surface in an intimate relationship. An outer sleeve overlies at least a portion of the bone probe and has a second manually-engageable element, which may be moved to position the sleeve against the proximal, outer surface of the bone entry opening hole, thereby permitting a determination of the size of the hole, which, in turn, permits determination of the size fastener to be used in surgical treatment of the bone. The device could be configured as two cylinders or partial cylinders which are "nested" one within the other, or in another embodiment, could be configured as two rule-like flatter elements similar to the configuration and sliding connectivity of a slide-rule device. In another embodiment, the elements may have a different complimentary shape, such as rectangular, for example.

In a preferred embodiment, the first manually-engageable elements comprise two ring-like elements, which are structured to receive the index and middle or ring fingers of the user and are adapted to be urged toward the bone for insertion of the probe through a bone hole and pull back away from the bone to thereby engage the bone-engaging portion with the distal exterior surface of the bone at the exit opening. The second manually-engageable element, which is preferably generally ring-shaped, is structured to be moved toward the bone to cause engagement between the outer sleeve and the bone adjacent the entry opening.

The three-finger, engageable elements, which may be rings, together also provide three-point fixation for control of the gauge for positioning and maintaining position of the device.

Dimensional indicia, as hereinafter defined, may be provided on the exterior surface of the bone probe and may be read adjacent to the proximal edge of the outer sleeve.

In a preferred embodiment, first manually-engageable elements are two in number and are positioned on opposite sides of the longitudinal axis of the bone probe and at about the same axial position on the bone probe. A second manually-engageable element associated with the outer sleeve may be disposed further from the bone-engaging portion of the bone probe than the first manually-engageable elements are from the bone-engaging portion of the bone probe. The second manually-engageable element is also preferably mounted to allow it to swivel about the longitudinal axis of the outer sleeve in order to facilitate the desired positioning of the thumb for controlled advancement of the outer sleeve. This is desirable because in the biomechanics of human three-point pinch (an action such as that of discharging a syringe or operating the device of the current invention), the thumb is naturally angled relative to that of the counteracting index and middle fingers. Allowing the thumb ring to swivel orients the plane of the ring engaged by the thumb to this natural and more mechanically efficient angle relative to the plane defined by the two rings engaged by the (a) index and (b) middle or ring fingers to allow optimal biomechanics of the hand for moving the sliding elements of the gauge.

A corresponding method is provided.

It is an object of the present invention to provide an effective depth gauge for measuring the depth of a bone opening in order to facilitate determination of the size fastener to be employed in surgical repair of the bone site and to provide a corresponding method.

It is another object of the present invention to provide adaptors, which permit retro-fitting beneficial features of the present invention into prior art devices.

It is a further object of the present invention to provide such apparatus and method wherein the direction-of-force application of the fingers employed in operating the device is in a physiologically-efficient direction utilizing optimal fine motor and sensory control portions of the hand.

It is yet another object of the present invention to provide such a system which eliminates the inefficiencies of the prior art devices by facilitating firm engagement of the apparatus and facilitating the movement required to effect the desired measurement.

It is yet another object of the present invention to provide such a system which employs enhanced maneuverability through efficient utilization of the biomechanics of the hand.

It is yet another object of the present invention to provide such a depth gauge and associated method, which is simple to maneuver, and facilitates accurate and easy reading of the indicated depth.

It is yet another object of the invention to provide such apparatus and related method which efficiently employs the inherent biomechanics of the human hand, so as to provide for effective controlled use.

It is yet another object of the present invention to provide such apparatus which is mechanically reliable, durable, and relatively inexpensive to manufacture.

It is yet another object of the present invention to provide such a depth gauge and associated method which is employable in such a manner as to permit the use of conventional surgical techniques.

It is yet another object of the present invention to provide such a system wherein the depth measurement can be such as to relate to solely the length of fastener employed alone or length of fastener required when additional hardware, such as plates, are employed.

These and other objects of the invention will be more fully understood from the following detailed description of the invention on reference to the illustrations appended hereto.

BRIEF DESCRIPTION OF THE DRAWINGS

FIG. 3 is a top plan view of a form of depth gauge of the present invention.

FIG. 4 is a front elevational view of the depth gauge shown in FIG. 3.

FIG. 5 is a cross-sectional view taken through 5-5 of FIG. 4.

FIG. 6 is a cross-sectional view taken through 6-6 of FIG. 4.

FIG. 9 is a perspective view of the modified form of outer elements, which provide the function of the inner bone probe of the first embodiment.

FIG. 10 is a perspective view of the element which functions as the outer sleeve in the embodiment of FIG. 9.

FIG. 11 is an elevational view of the elements of the embodiment of FIGS. 9 and 10 shown assembled.

FIG. 12 is a top plan view of a further embodiment of the inner probe.

FIG. 13 is a front elevational view of the inner probe of FIG. 12.

FIG. 14 is a left side elevational view of the probe of FIGS. 12 and 13.

FIGS. 15 through 17 show the outer barrel for use with the embodiment of FIGS. 12 through 14.

FIG. 15 shows a front elevational view.

FIG. 16 shows a top plan view of outer barrel of this embodiment.

FIG. 17 is a left side elevational view of the outer barrel of FIGS. 15 and 16.

FIG. 18 is a cross-sectional illustration of the outer barrel of this embodiment taken through 18-18 of FIG. 15.

FIG. 19 shows an exploded view of a further embodiment of an adaptor securable to the inner probe of a prior art device.

FIG. 20 shows a perspective view of an adaptor for the outer barrel employable with the assembly of FIG. 19.

FIG. 20(a) shows a perspective view of a modified form of manually-engageable ring and securing member.

DESCRIPTION OF THE PREFERRED EMBODIMENTS

Figure 1:
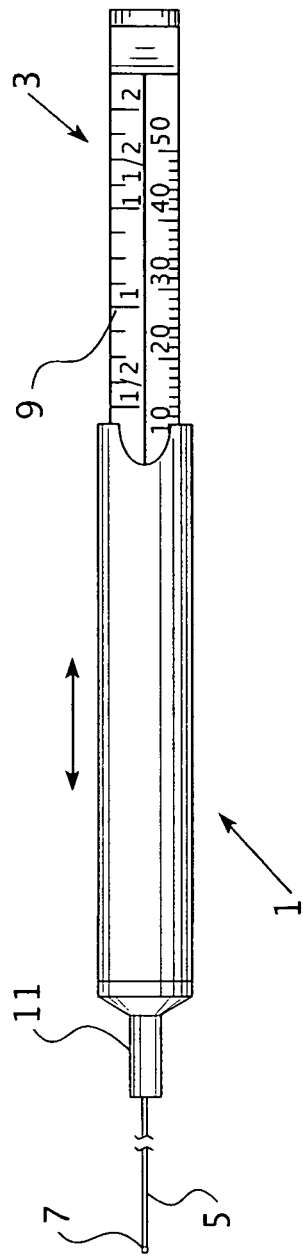
FIG. 1 is a top plan view of a prior art form of gauge.
Figure 2:
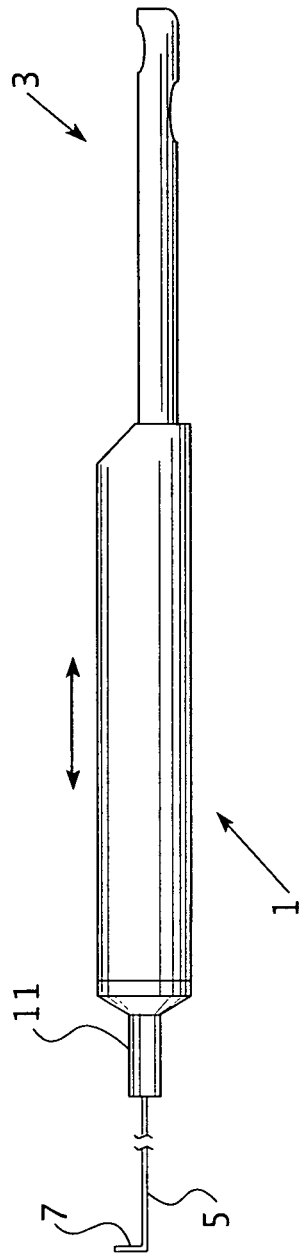
FIG. 2 is a front elevational view of the prior art gauge of FIG. 1.

As employed herein, the term "patient" means a member of the animal kingdom, including human beings.

As employed herein, the term "dimensional indicia" means visually perceptible markings, which are related to the depth of the bone as determined by the interaction between a bone probe and an outer sleeve and shall expressly include a ruler-like scale in whatever units are desired, and/or graphic elements and/or color indicators, as well as combinations thereof.

Referring to FIGS. 3 and 4, there is shown an elongated inner bone-engaging probe 2 which has an outer sleeve 4 overlying portions thereof and structured for relative sliding movement between the inner bone-engaging probe 2 and the outer sleeve 4. The distal end of the outer sleeve 4 would typically be tapered to an elongated, rounded tip 5. The outer sleeve 4 preferably has an axial length shorter than the bone probe 2. Among other things, this facilitates ready visual access to extended dimensional indicia positioned on the exterior of the bone probe 2. In the form shown, the inner bone-engaging probe has a projecting narrow distal portion 8, which, in the form shown, terminates in a hook 10. The narrow distal portion comprising the inner probe width and reentrant hook width together may have a dimension X of about 0.5 millimeters to 5 millimeters, but this dimension may vary depending upon the size of the bone which is being subjected to medical treatment. The length of the elongated portion of the narrow probe will typically have a dimension Y of approximately 2 to 10 centimeters depending on the size of the bone being treated.

The bone probe has a plurality of manually-engageable elements fixedly secured thereto. In the form shown in FIGS. 3, 4, 5, and 6, a pair of generally ring-like first manually-engageable elements 20, 22 are secured to the bone probe 2 by a connector 24. The generally ring-like, manually-engageable elements 20, 22 are in the form shown disposed on opposite sides of the central axis of the elongated bone probe 2 at generally the same axial position. The manually-engageable elements 20, 22 define respectively openings 30, 32 which are structured to receive the fingers of the user. Fixedly secured to the outer sleeve 4 by connector 34 is a manually-engageable element 36, which, in the form shown, is generally circular and has an opening 40 sized to receive a thumb of the user. Element 36 is connected by a swiveling mechanism that allows it to spin 360 degrees around the long axis of the outer barrel. The elements 20, 22, 36 may be generally circular and have an internal diameter of about 0.75 to 1.25 inches. As shown in FIG. 3, the exterior of bone probe 2 has dimensional indicia 44, which, in the form shown, has a numerical scale. As will be set forth hereinafter, in the distal end 5 of the outer sleeve 4 is an engagement with the proximal outer surface of the bone adjacent to the hole. The proximal end 52 of the sleeve will be aligned with a portion of the dimensional indicia thereby providing a determination of the length of fastener to be employed.

The position of the second manually-engageable element 36, which is spaced from a position of manually-engageable elements 20, 22, must be sufficient to permit the thumb in engagement with manually-engageable element 36 to have a free range of movement in both axial directions so as to accommodate the range of excursion needed for the outer shell 4.

Figure 7:
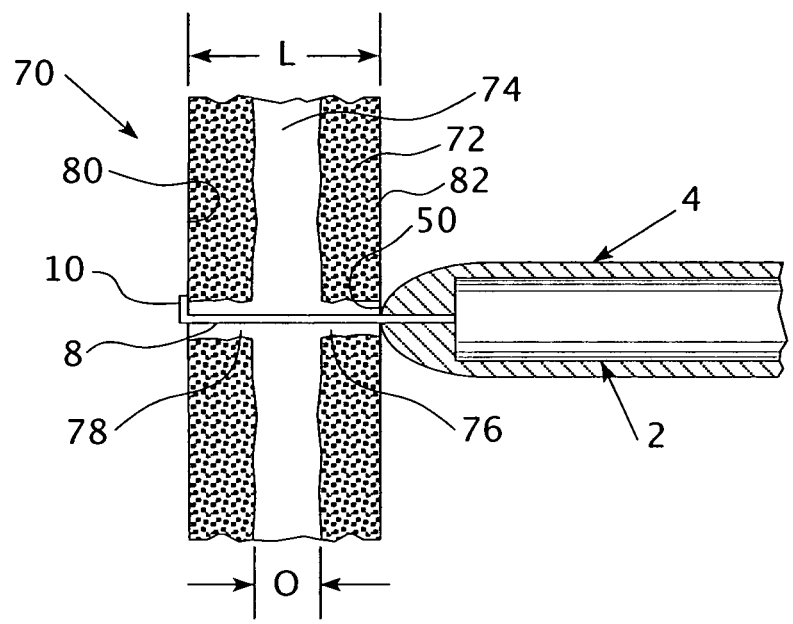
FIG. 7 is a cross-sectional view showing a portion of a bone with the bone-engaging portion of the assembly.
Figure 8:
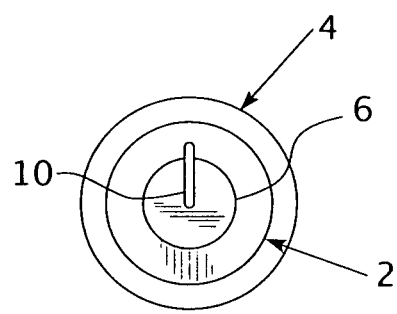
FIG. 8 is an end elevational view of the distal portion of the gauge.

Referring to FIG. 7, after first passing the probe 8 through the bone hole, the withdrawing of the narrow distal portion 8 to engage the hook 10 can best be accomplished by gentle flexion of the fingers within rings 20, 22 to provide maximum feel of when engagement of the reentrant hook 10 with the distal exterior surface 80 of the bone 70 has been achieved. Generally, the volar side of the fingertips would be engaged within and against the rings 20, 22, 36 during the main phase of movement of the corresponding probe 2 and sleeve 4 as a highly-developed tactile sense exists in this portion of the hand/fingers. Once the reentrant hook 10 is in place, slight force applied by flexion of the tips of the fingers can maintain the desired intimate contact.

In general, the bone probe 2 and the outer sleeve 4 are preferably hollow so as to, with respect to the bone probe 2, reduce the material costs and weight of the same, and as to the outer sleeve 4, to permit relatively intimate contact between the inner surface of the outer sleeve 4 and the outer surface of the bone probe 2. It will be appreciated that, if desired, the bone probe 2 need not be hollow, but the outer sleeve 4 should be to permit the bone probe 2 to be disposed in and moved within the outer sleeve. The bone probe 2 and outer sleeve 4 may be made of any suitable material, such as an appropriate metal, for example, stainless steel or aluminum or suitable resinous material all of which are sterilizable. Usually, the elements of the gauge and other similar instruments are manually cleaned in some type of cleaning solution combined with scrubbing and are then sterilized either by heat or with a sterilizing solution. For metal instruments this is usually just steam heat autoclaving.

Referring to FIGS. 5 and 6, which show cross-sections taken through 5-5 and 6-6 of FIG. 4, FIG. 5 shows the bone probe 2 which defines a recess 60 and, in the form shown, has a generally-circular configuration. This might be a half-circle also if the inner barrel is more of a half-cylinder and would be rectangular if a "slide-rule like" design was used Elements 2 and 4 would be flatter in such a design. Cylinders or partial cylinders, such as half cylinders would be stronger mechanical shapes generally, but are not the only alternative. Connector 24 is secured at its ends to manually-engageable element 20 and manually-engageable element 22. The outer surface 62 of the bone probe 2 is in intimate contact with the inner surface 64 of the outer sleeve 4. As shown in FIGS. 3 and 4, outer sleeve 4 has a tapered end 5 having an opening therethrough for passage of distal portion 8.

Referring to FIG. 7, in practice of the method, a bone 70 is addressed, which in practice, is usually essentially a thick-walled hollow cylinder, which has an outer cortex wall 72 and an inner medullary cavity 74. In practicing the method, entry hole 76 and exit hole 78 are provided in wall 72 in generally-aligned relationship by pre-drilling through the bone. The narrow distal portion 8 containing the hook 10 is passed through the same and in a manner described hereinafter is partially withdrawn so as to cause the reentrant hook 10 to engage the exterior surface of wall 72.

The bone exit hole 78 and bone entry hole 76, which are sufficiently large in diameter to permit the reentrant hook to pass therethrough freely, are aligned with the instrument and with the narrow distal portion 8 passed through the hole with the hook 10 being on the distal side of the bone 70. By applying a force to the inner barrel with elements 20, 22 to maintain the probe 8 against the sidewall of the hole and also applying a withdrawing force away from the bone and toward the user to manually-engageable elements 20, 22, the elongated bone probe 2 will cause the hook 10 to engage a rear surface, such as 80, of the bone wall 72, thereby resisting withdrawal of the narrow distal portion 8 from the bone 70. While maintaining this interengagement, the thumb is employed to move the barrel 4 toward the proximal surface 82 of the bone 70 until engagement is achieved. While holding these positions, one then looks at the proximal end 52 of the barrel 4 and reads the dimensional indicia 44 (FIGS. 3 and 4) in order to determine what length of fastener should be employed with the specific bone 70. To remove the gauge, the force of the probe 8 against the sidewall of the bone hole is relaxed, and the manually-engageable elements 20, 22 are then moved toward the bone, so as to move hook 10 out of engagement with surface 80 at which point the narrow distal portion 8 can be passed outwardly through holes 78, 76, thereby withdrawing the instrument which may then be used for additional similar measurements needed to complete the case. After the surgery case is completed, the device can then be subjected to sterilization or an appropriate cleansing solution to prepare it for further use in other surgeries. If a disposable design is used, the gauge could be discarded after the surgical case is complete.

While in FIG. 7, the bone 70 has been shown as being hollow having an inner medullary cavity 74, it will be appreciated that some bones will be of solid cross-section. Also, in some instances, measurement may be made on cadaver bones, as well as animal bones.

The probe 2, outer shell 4, rings 20, 22, 36, and their arms and attachment mechanisms could be made of various materials including various metals, plastics, composites, or other suitable materials. The same material could be used for all parts, or some portions could be made of one material and other portions of a different material. In practice, a material, such as stainless steel, is preferred for its availability, cost, strength, durability, ease of cleaning, and ability to be sterilized. Metallic components also have the advantage of being able to be easily visualized radiographically, to check the position of the probe or other portions of the gauge during measurement, and also to locate all, or a portion, of the instrument should it become lost in a wound or should a portion break off within a wound. It is also preferred that the design and materials used allow easy sliding of the inner and outer barrels over each other with little friction. Designs in which the probe portion is metallic and the other main components of the inner and outer sleeves and ring devices are a different material, such as plastic, could provide a design in which part or all of the gauge is disposable or designed for single-case use.

One or all of the rings 20, 22, 36 could be made as an integral part of the corresponding probe 2 or shell 4 or could be made attachable by a variety of coupling mechanisms including such things as fittings and screws, direct threading of one part onto another, press or mated fit or other mechanisms. Likewise, portions of the gauge, such as the arm or outrigger used for the single ring on the outer barrel, could be integral or attachable. Designs in which the parts are attachable would facilitate dismantling the apparatus for cleaning and or replacement or interchange of an individual damaged portion.

In addition to devices, which incorporate the novel features of the present invention into a depth gauge in integral fashion, the ring elements 20, 22, 36 and adaptive could also be structured to mate with existing gauges by a variety of coupling mechanisms, which would transform existing gauges such that they could be manipulated and be made in the manner of the present invention (see FIGS. 19 and 20). Such elements could be made in such a way as to be disposable and for single case use or could be made in a fashion to render them reusable after appropriate cleansing and sterilizing.

The rings 20, 22, 36 are positioned in such a way that they do not abut each other or other portions of the device or interfere with the excursion of the sliding portions of the gauge.

The rings 20, 22, 36 could be of various sizes in respect to both diameter and ring height. One size of ring could be used for all three rings on a gauge, or the different rings could be sized differently on the various parts of the gauge, such as using one size for the single ring on the outer barrel and a different size for the two rings on the inner barrel. The rings should be sized to accommodate most human hands. Typically, the rings would all be of the same size.

It will be appreciated that depth gauges of various sizes will be employed depending on the size of the bone. It is desired that the narrow distal portion 8 be so dimensioned so as not to project substantially a great distance beyond the exit hole 78 into tissue on the distal side of the bone.

Movement of the outer barrel 4 toward the bone is preferably achieved by a combination of flexing and adducting the thumb of the user within ring 36. The fine neuromuscular control by the human thumb coupled with the excellent sensory feedback by the tip of the thumb engaged in the ring 36 facilitates precise control.

Figure 10A:
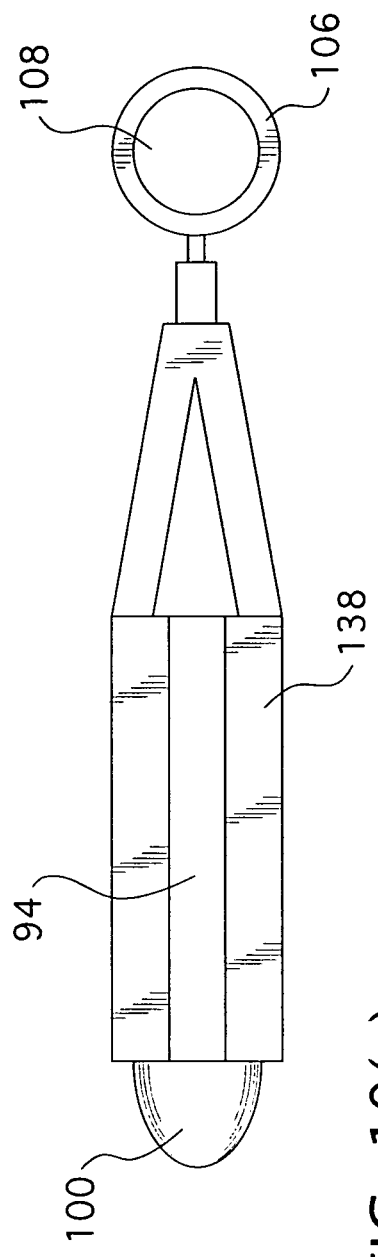
FIG. 10(a) is a bottom plan view of the element of FIG. 10.

Referring to FIGS. 9 through 11, another embodiment of the invention will be considered. In this embodiment, the structure, rather than being generally cylindrical, has a generally-flat configuration. As shown in FIGS. 10, 10(*a*), and 11 the outer sleeve or second element 90 has generally-parallel upper and lower surfaces 92, 94 and elongated longitudinal upwardly opened recess 96. The second element 90 terminates in a tapered nose portion 100, which has an axial passageway 102 for passage of the probe portion 104 (FIG. 9) through. In the form shown, a manually-engageable portion 106, which as illustrated, is a continuous ring defining opening 108 for passage of the thumb of the user therethrough, is provided.

Referring in greater detail to FIG. 9, the probe 104 terminates in a generally-hook shaped portion 110, which is structured to engage the distal surface of the bone adjacent to the exit opening. A body portion of the probe or first element 112 contains measuring indicia 114 and has a pair of first, manually-engageable portions 120, 122 connected thereto by element 124. In the form shown, first, manually-engageable portions 120, 122 are continuous closed rings, which define openings 130, 132, respectively.

As shown in FIG. 11, the assembly provides a generally-flat structure which has the second, manually-engageable portion 106 spaced further from the probe hook 110 than the first, manually-engageable portions 120, 122. The second, manually-engageable portion 106 is, in the form shown, rotatably mounted as a result of pivot member 134, which is rotatably secured within generally upwardly projecting part of flange 136 of connector 138, which, in turn, is fixedly secured to the undersurface of outer element 90 and involves the use of a partial sleeve, as contrasted with the hollow cylinder disclosed in connection with FIGS. 3 and 4.

In the embodiment of FIGS. 12 through 14, it will be seen that a probe 140 terminating in a hook 142 is fixedly secured to a body portion 144, which has on its upper surface calibrations indicia 146. At the proximal end of the body portion 144 are a pair of manually-engageable elements 150, 152, which in the form shown, are closed rings defining finger receiving openings 154, 156 respectively. The rings 150, 152 are connected to the body 144 by connecting element 160. As shown in FIG. 14, the probe element has a body 144 which in cross-section is in the shape of a hemisphere having a downwardly-facing convex surface 162.

Referring to FIGS. 15 through 18, the cooperating outer barrel portion for use with the probe portion of FIGS. 12 through 14 will be considered. The outer barrel terminates in a tapered end 170 which defines a passageway 172 through which the probe portion 140 will pass. The body portion 174, as shown in FIG. 18, has a generally-hemispherical configuration with an upwardly opened recess 176 and a pair of upper longitudinally oriented flanges 180, 182. The flanges 180, 182 are preferably elongated and substantially continuous. The body portion 174 may be made of any suitable material, such as stainless steel, for example. Secured to the undersurface of the body is connecting rod 184, which is fixedly secured at its proximal end 186 to retainer 188 which is secured to ring 190 and defines finger receiving opening 192. Pivot pin 194 is fixedly secured to ring 190 and passes through retainer 188. It will be appreciated that ring 190 is structured to receive the thumb of the user and for efficiency of use, is rotatably secured to retainer 188 so as to permit rotation of the ring generally about the orientation of the long axis of the outer barrel.

FIG. 17 is an end elevational view showing the distal end.

FIGS. 19 and 20 show representative adaptors, which could be made incorporating the features and function of the ring elements. These could be employed to secure manually-engageable portions 203, 204, 216 to existing prior art devices, such as 195. These adaptors, in a manner known to those skilled in the art, could be attached by a variety of mechanisms including screw-on, press-fit or fittings otherwise secured to depth gauges of the type of the prior art to produce functioning in these prior art gauges like that of the present invention.

Referring to FIGS. 19 and 20, a prior art device 195 having an inner probe 199 provided with measuring indicia 200 and a projecting probe 197 terminating in a hook 198. Outer sleeve 194 terminates in a nose portion 196. Inner probe 199 is slidably received within outer sleeve 194. The adaptors of FIGS. 19 and 20 facilitate retro-fitting the benefits of the present invention into prior art devices. In the form shown in FIG. 19, the device 195 has a sleeve portion 194, which terminates in a tapered portion 196, and inner probe has a projecting probe 197, which has at its distal end a hook 198. A generally-flat portion 199, which projects in the proximal direction, is slidably disposed within sleeve portion 194. Measuring graduations 200 are provided on the upper surface of the plate-like portion of inner probe 199. An adaptor element 201 has a passageway 202 provided with a pair of rings 203, 204 defining finger receiving recesses 205, 206, respectively, secured thereto by connectors 207, 208, respectively. In assembling the unit for use, adaptor element 201 is moved in the direction of the arrow A so that end 209 of inner probe 199 is received within passageway 202 in intimate friction fit contact, while permitting separation thereof.

Referring to the adaptor portion of FIG. 20, the outer barrel curved body portion 210 defines an upwardly open recess 212, which is of complementary configuration to at least a portion of the exterior of the sleeve portion 194, so as to permit snap fit interengagement. The material out of which adaptor curved body portion 210 is made is preferably a resilient material, such as plastic or an appropriate metal, and has a circumferential extent great enough to permit intimate snap fit engagement with the exterior surface of sleeve portion 194. It will generally be preferred to have the adaptor curved body portion 210 extend circumferentially at least about 180 degrees. Connecting rod 214 has one end 217 secured to the undersurface of outer barrel 210. Connecting rod 214 has a ring 216 defining the finger receiving opening 218, rotatably secured thereto for rotation about an axis generally aligned with the longitudinal axis of the adaptor body portion 210 through connector block 220 and connector 222.

If desired, ring 216 and connector 222 may be secured to connector block 220 by an enlarged head 228 on the end of connector 222. It may also be removably secured to connector block 220 as by employing, for example, the ring 216' shown in FIG. 20(a) having opening 218' in connector 222' with a threaded portion 223. The connector 222' will be dimensioned so as to pass through an opening in connector block 220 and may be secured in place by nut 225.

Figure 21:
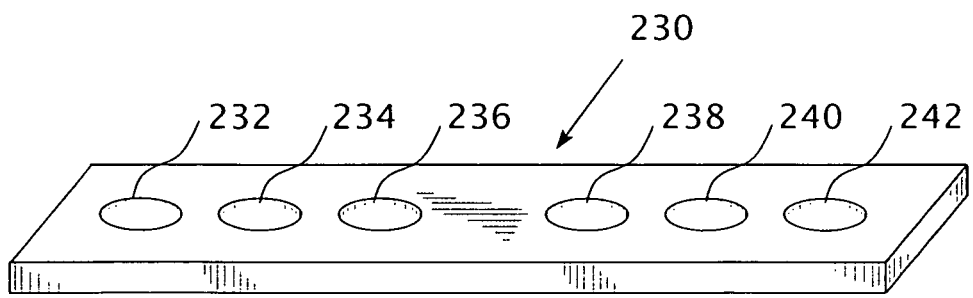
FIG. 21 shows a perspective view of a type of bone fixation plate, which is employed in some circumstances to reinforce the bone during the healing process.

FIG. 21 shows a conventional bone fixation plate 230, which is a generally-rectangular cross section and has a plurality of fastener receiving openings 232, 234, 236, 238, 240, 242. Usually, measurement in this context is effected by the distal or "nose" portion of the outer barrel being tapered to interdigitate with a hole 232, 234, 236, 238, 240, 242 in a plate so that the outer barrel is brought down to the point of the plate where the screwhead will sit and thus accommodate for the thickness of the plate. In practice, often a screw of 1 or 2 millimeters longer than that measured is used to ensure that it traverses the whole thickness of the plate and bone and slightly protrudes from the far end or exit bone hole. The length of screws is usually checked by X-ray while in the operating room to confirm that all screws are of appropriate length and that no mis-measurement has occurred.

Figure 22:
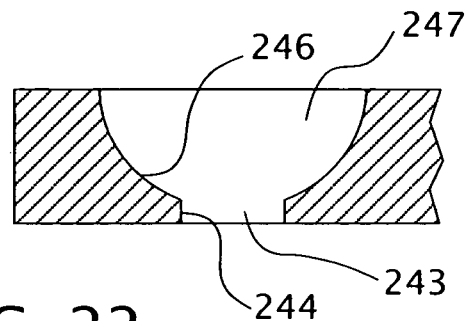
FIG. 22 shows a detail of a cross section of an opening of a bone fixation plate, showing an enlarged recessed portion for receipt of a screw head.
Figure 23:
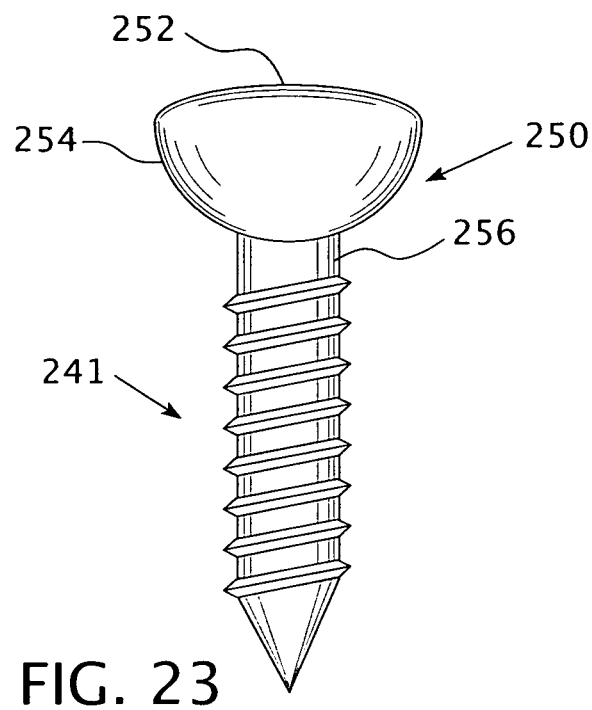
FIG. 23 shows a type of screw usable in bone fixation with a bone fixation plate.

Referring to FIGS. 22 and 23, a detail of one of the openings, such as 232, is illustrated. It is noted that there is a relatively narrow portion of the opening defined by annular wall 244 and a generally-outwardly curved, tapered portion of the wall 246, defining an enlarged portion of the opening 247. Referring to FIG. 23, there is shown a conventional screw fastener 241, which has a head portion 252 and a curved generally-downwardly tapered exterior surface 254. The shank portion 256 is contoured and dimensioned so as to be received within a portion of the hole 243, defined by wall 244 and the curved tapered portion 254 is shaped and dimensioned so as to be received within the portion of the opening defined by wall 246.

Figure 24:
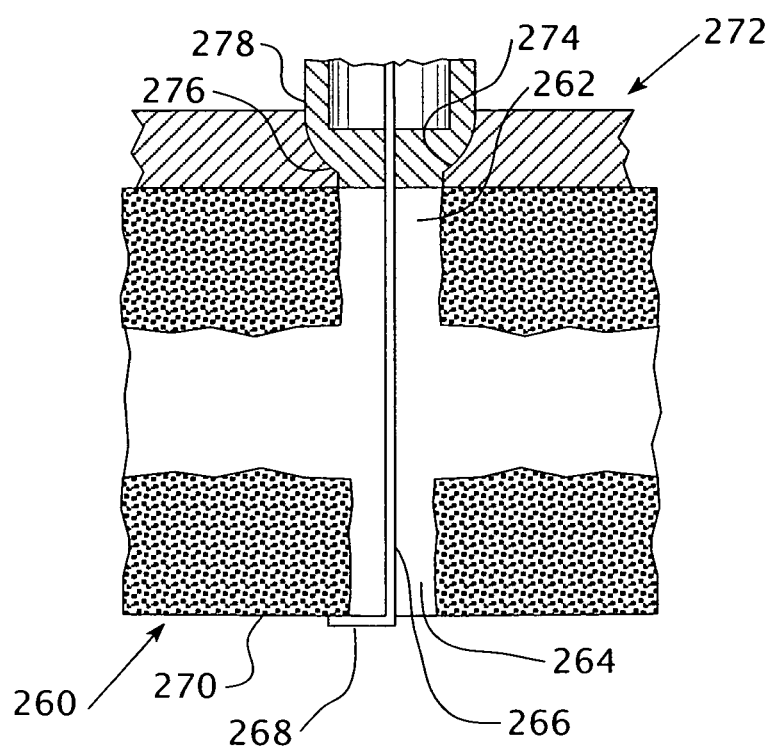
FIG. 24 is a partial cross sectional view showing the outer shell tapered portion engaged within a plate, which is disposed against a bone.

Referring to FIG. 24, there is shown a bone 260 having an entry hole 262 and an exit hole 264 through which has passed a probe 266 having its hook-like distal end 268 engaging with an outer surface 270 of the bone 260. A portion of a bone fixation plate 272 has a hole 274 within which is received the tapered portion 276 of the outer shell 278. In this manner, the determination of fastener length needed to pass through and secure the bone fixation plate 272, as well as extend into the bone to the desired depth may be determined.

Figure 25:
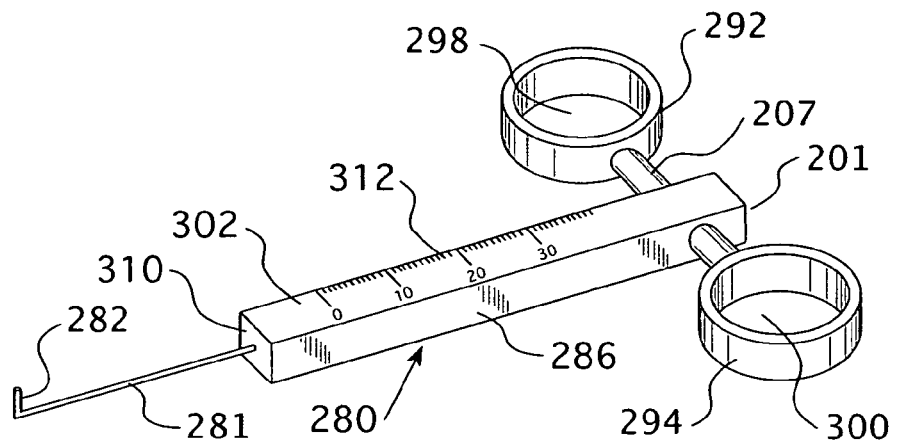
FIG. 25 is a perspective view of another embodiment of a bone probe of the present invention.
Figure 26:
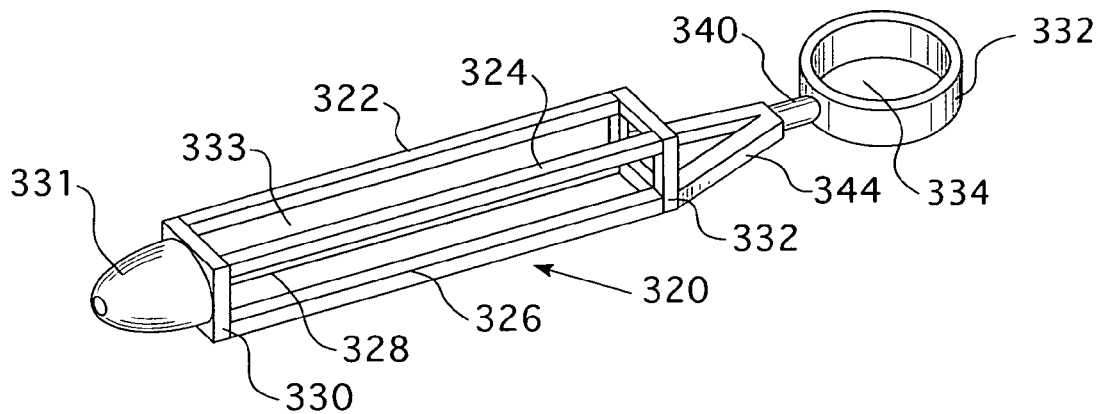
FIG. 26 is a perspective view of an outer component structured to be operatively associated with the bone probe of FIG. 25.
Figure 27:
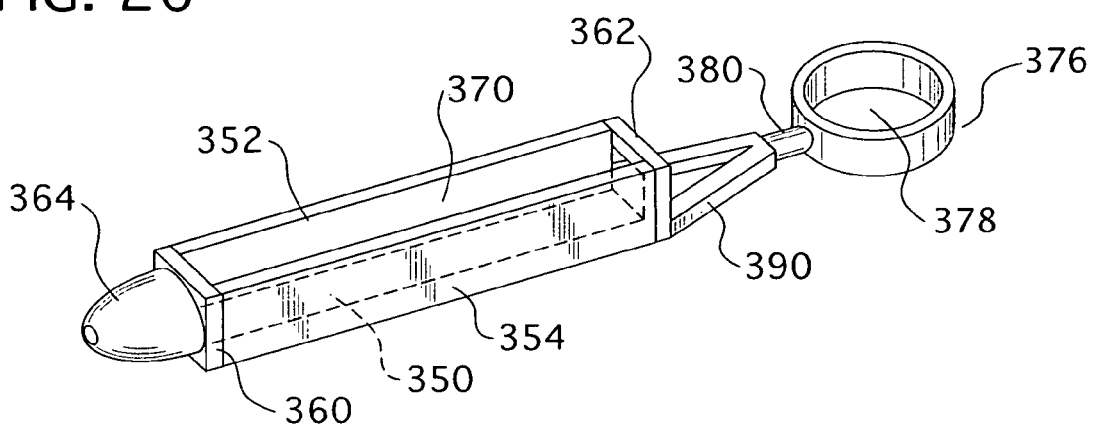
FIG. 27 is a perspective view of another embodiment of an outer component of the present invention also suitable for operating in combination with the bone probe of FIG. 25.

Referring to FIGS. 25 through 27, a further embodiment of the invention will be considered. FIG. 25 shows a bone probe 280, which has a projecting, bone-engaging portion 281, which terminates In a hook-like portion 282. The body 286 is of generally-rectangular cross-section and has fixedly-secured thereto, a pair of manually-engageable portions 292, 294, which, in the form shown, are ring-like and define finger-receiving apertures 298, 300, respectively. The body portion 280 consists of an upper surface 302, which is generally parallel to a lower surface (not shown) and a pair of side surfaces 286 and a generally-parallel surface (not shown). Each of the four surfaces are generally rectangular and cooperate with a rectangular-shaped end wall 310. The body 286 may be of solid or hollow construction, as desired. Dimensional indicia 312 are provided on the upper surface 302.

An outer element 320, which may function with the inner bone probe element 280 of FIG. 25, is shown in FIG. 26. It will be appreciated that the outer element 320 is defined by four, elongated, generally-parallel corner members 322, 324, 326, 328, which are secured at opposed ends to generally-rectangular end members 330, 332. A projecting nose portion 331 has an opening to permit probe 281 to pass therethrough. The interior space is so configured so as to permit the bone inner probe element 280 to be axially inserted into space 333 from the right and moved toward the left in FIG. 26, so that the probe 281 projects from the left side thereof, while maintaining intimate interrelationship between the bone probe 280 and the outer element 320. A second, manually-engageable portion 332, which, in the form shown, is a generally ring-like configuration having a thumb receiving opening 334, is structured to pivot about pin 340, which is secured to connector 344. It will be appreciated that the components shown in FIGS. 25 and 26, when assembled, permit the device to function as in previously-described embodiments.

Another embodiment of the outer member suitable for use with the bone probe of FIG. 25 is shown in FIG. 27, wherein a base wall 350 cooperates with a pair of upstanding, generally-parallel side walls 352, 354 and end reinforcing members 360, 362 to define a recess 370 within which the inner bone probe element 280 of FIG. 25 may be introduced by sliding movement from right to left. A projecting nose 364 has an opening for passage of probe 281 therethrough. A second, manually-engageable portion 376 is a generally ring-like form having an opening 378 for receipt of the user's thumb while permitting pivoting about the longitudinal axis of connector 380, which is secured to connector 390.

It will be appreciated that the three manually-engageable portions, which are in the preferred embodiment, are three rings, provide three point fixation which enhances control of the gauge for general positioning and stably holding the same.

While flanges or partial rings or posts could be employed in place of the full rings 20, 22, 36 described herein, the full rings are preferred. These alternate approaches, while usable, would not provide appropriate function, as forces could not be exerted in both forward and backward or multiple directions, as is preferred in order to provide superior control of the instrument.

It would not be desirable to switch the two-ring and one-ring positions so that two rings are associated with the outer barrel and the single ring with the inner barrel/probe. In this case, a single ring would be attached to the proximal end of the inner barrel and two rings attached to the outer barrel. This would result in the main movements of the barrels being controlled by extending the fingers and thumb rather than flexing them to move the barrels. After inserting the probe into the bone hole, the thumb would have to extend to withdraw the probe and "hook" its end while the thumb in the single ring would also have to maintain force of the probe against the side walls of the bone hole. The index and middle fingers would then have to extend to advance the outer barrel down to the surface of the bone. Extension of the fingers and thumb is less highly controlled than flexion of these digits. The pressure perceived by resistance of the movements and which provides the feedback necessary to the accuracy of the movements is also directed to the relatively less sensitive dorsum or back side of the digits rather than the very sensitive volar side thus contributing to less finely controlled movement. The probe would also be controlled and maintained in position by a single digit (the thumb), which is more awkward and less stable than with the configuration of the present invention. This alternative configuration would be a much less desirable mode of function for a depth gauge. Syringes and other surgical instruments referenced earlier in the prior art are configured in this way, i.e., with a single ring and the thumb controlling the inner barrel portion of the device and this is appropriate as in those cases the inner barrel is the "working" and mobile piece being advanced, being the plunger in the case of a syringe and extraction devices or probing devices in other cases.

While certain lengths of probe 8 have been illustrated, it will be appreciated that different lengths, which correlate with the indicia in size, may be employed.

While it will be appreciated that for convenience and clarity of illustration, several different shapes of outer sleeve tip, such as 5 in FIGS. 3 and 4 or 276 of FIG. 24, for example, have been shown, one skilled in the art may provide other configurations, which provide the desired functionality.

Whereas particular embodiments of the invention have been described herein for purpose of illustration, it will be evident to those skilled in the art that numerous variations of the details may be made without departing from the invention as set forth in the appended claims

The invention claimed is:

1. Apparatus for measuring bone depth comprising:
   an elongated inner bone probe structured to extend through openings in a bone,
   said inner bone probe terminating in a bone-engaging portion for engaging a distal portion of said bone adjacent an exit opening in said bone,
   said inner bone probe having a plurality of first manually-engageable elements secured to said inner bone probe for effecting movement of said inner bone probe by a user employing the volar sides of the user's fingers,
   said inner bone probe being structured to have a distal portion pass through an entry opening in said bone and engage said distal portion adjacent to an exit opening in said bone with said engagement being maintained by manual engagement of said first manually-engageable elements by the volar sides of said user's fingers and a withdrawing force applied thereto by said user's fingers in a direction generally away from said bone and toward the user's hand,
   an outer sleeve overlying at least a portion of said inner bone probe,
   said outer sleeve having a second manually-engageable element for engagement and movement of said sleeve by a user employing the volar side of said user's thumb,
   said outer sleeve being structured to be moved to a position engaging said bone or a fixation plate adjacent an entry opening in said bone by manually engaging said second manually-engageable element by the volar side of said user's thumb and pushing said outer sleeve toward said bone,
   said user's fingers and said user's thumb being on the same hand of said user,
   said first engageable elements having openings for receiving said user's fingers,
   said second manually-engageable element having an opening for receipt of said user's thumb,
   said first and second manually engageable elements being generally ring-shaped,
   said apparatus being structured to effect during said measurement movement of said first manually engageable ring shaped elements in the opposite direction of movement from said second manually engageable ring shaped element,
   said inner bone probe and said outer bone probe being structured to move along a longitudinal axis of said apparatus, whereby said apparatus is structured to permit holding said apparatus while effecting engagement of said first manually-engageable elements by the volar sides of said user's fingers to apply a withdrawing force to said inner bone probe in a direction toward said user's hand to urge said bone engaging portion into intimate contact with said bone adjacent said distal portion of said bone while concurrently with applying said withdrawing force engaging, said second manually-engageable element by the volar side of said user's thumb and pushing said second manually-engageable element to cause said outer sleeve to engage said bone or fixation plate adjacent an entry opening in said bone to permit the bone depth to be determined.

2. The apparatus of claim 1 including
   said first manually-engageable elements having a pair of said manually-engageable elements with one being disposed on each side of the central axis of said bone probe.

3. The apparatus of claim 1 including
   said bone-engaging portion having a hook for engaging said distal portion of said bone.

4. The apparatus of claim 1 including
   said outer sleeve having a distal end structured to engage a proximal portion of said bone adjacent an entry opening in said bone or a hole in a bone fixation plate adjacent to said hole in said bone.

5. The apparatus of claim 3 including
   said bone probe having dimension indicia on the exterior thereof.

6. The apparatus of claim 5 including
   said outer sleeve being structured when moved to a position having its distal end engage an outer proximal portion of said bone or a fixation plate adjacent an entry opening in said bone to align the outer sleeve proximal end with said dimensional indicia, whereby the length of a fastener needed to secure said bone can be determined.

7. The apparatus of claim 5 including
   said second manually-engageable element being disposed farther from said bone than are said first manually-engageable elements.

8. The apparatus of claim 7 including
   said second manually-engageable element having a continuous ring defining an opening for receipt of a user's finger.

9. The apparatus of claim 1 including
   employing two said first manually-engageable elements with one disposed on each side of the central axis of said bone probe.

10. The apparatus of claim 9 including
    said first manually-engageable elements being substantially coplanar with each other.

11. The apparatus of claim 10 including
    said first manually-engageable elements being disposed generally at the same axial position of said bone probe.

12. The apparatus of claim 5 including
    said first manually-engageable elements being structured to receive an index finger and a middle or ring finger of said user.

13. The apparatus of claim 1 including
    said apparatus being structured to be employed on the bone of a patient.

14. The apparatus of claim 13 including
said apparatus being structured to be employed on a patient who is a living human being.

15. The apparatus of claim 12 including
said second manually-engageable element being rotatably mounted to permit it to swivel generally around the longitudinal axis of the outer sleeve.

16. The apparatus of claim 1 including
said second manually-engageable element being rotatably mounted.

17. The apparatus of claim 1
said outer sleeve terminating in a distal end which is tapered in a direction generally away from said second manually-engageable element, and
said tapered end having a passageway for passage of said bone-engaging portion of said inner bone probe.

18. The apparatus of claim 1
said first manually-engageable ring-shaped elements being structured to receive the user's index and middle fingers and
said second manually-engageable element being structured to receive said user's thumb on the same hand as said fingers.

\* \* \* \* \*